US00PP31433P2

(12) United States Plant Patent
Hansen

(10) Patent No.: US PP31,433 P2
(45) Date of Patent: Feb. 4, 2020

(54) ***HEUCHERA* PLANT NAMED 'PEACHBERRY ICE'**

(50) Latin Name: ***Heuchera* hybrid**
Varietal Denomination: Peachberry Ice

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 16/350,003

(22) Filed: Sep. 10, 2018

(51) Int. Cl.
*A01H 5/02* (2018.01)
*A01H 6/80* (2018.01)

(52) U.S. Cl.
USPC ..... Plt./440
CPC ..... *A01H 6/80* (2018.05)

(58) Field of Classification Search
USPC ..... Plt./440
CPC ..... A01H 6/80; A01H 5/02
See application file for complete search history.

*Primary Examiner* — Keith O. Robinson

(57) ABSTRACT

The new and distinct hybrid of *Heuchera* plant named 'Peachberry Ice' with large foliage having rounded apices and lobes, leaf blades begin the season reddish-peach colored and develop to orangish-red with silverish overlay between the veins. Leaf blades are shallowly dissected with tiny sharp tips and ruffled margin. Flowers are on stiff, upright, wine-colored branched panicles just above foliage and give a pale pink effect from calyces. The new plant is vigorous and produces large broadly-mounded clumps.

2 Drawing Sheets

Botanical denomination: *Heuchera* hybrid.
Variety denomination: 'Peachberry Ice'.

BACKGROUND OF THE INVENTION

The present invention relates to a new and distinct cultivar of Coral Bells in the Saxifragaceae family and given the cultivar name of 'Peachberry Ice'. *Heuchera* 'Peachberry Ice' was hybridized by the inventor on Feb. 26, 2015 at a wholesale perennial nursery in Zeeland, Mich., USA. The seed or female parent was the proprietary unreleased hybrid known as 12-120-1 (not patented) and the pollen or male parent was 'Paprika' U.S. Plant Pat. No. 24,575.

*Heuchera* 'Peachberry Ice' was first selected in the summer of 2016 and assigned the breeder code 15-106-116 through the remaining evaluation process where it passed final evaluation in the fall of 2017 from among many other seedlings from the same cross and hundreds of other crosses. *Heuchera* 'Peachberry Ice' has been asexually propagated by division at the same nursery in Zeeland, Mich. in 2016 and by sterile, shoot-tip, tissue culture propagation, and the resultant plants have remained stable and continued to exhibit the same characteristics as the original plant for multiple generations.

No plants of *Heuchera* 'Peachberry Ice' have been sold, in this country or anywhere in the world, prior to the filing of this application, nor has any disclosure of the new plant been made prior to the filing of this application with the exception of that which was disclosed within one year of the filing of this application, and was either derived directly or indirectly from the inventor.

BRIEF SUMMARY OF THE INVENTION

The nearest comparison varieties include: the male parent 'Paprika', 'Rio' U.S. Plant Pat. No. 24,273, and 'Georgia Peach' U.S. Plant Pat. No. 19,375. 'Paprika' is smaller and shorter in foliage and in flower heights and mound width, is less vigorous and has smaller foliage with less ruffled margin and less reddish coloration. 'Georgia Peach' has more orangish foliage coloration and taller panicles. 'Rio' is smaller and shorter in foliage and flowering heights and mound width, is less vigorous and has smaller foliage with deeper reddish coloration and without the lighter silver overlay between the leaf veins. The female parent had more of a chocolate-colored foliage with more rounded leaf blades that were less ruffled. 'Mocha' U.S. Plant Pat. No. 18,386 has much darker mahogany colored foliage on more compact plants. The proprietary selection of *Heuchera hallii* in the parentage has green compact green foliage with short dense cream-colored flowers.

*Heuchera* 'Peachberry Ice' differs from its parents as well as all other coral bells known to the applicant in the following combined traits:

1. The large foliage has rounded apices and rounded lobes.
2. Large leaf blades begin season reddish-peach coloration and just before flowering develop into orangish-red coloration with silverish overlay between the veins.
3. Leaf blades are shallowly dissected with apices rounded with tiny sharp tips and ruffled margin.
4. Flowers provide a pale pink effect from calyces with white petals.
5. Stiff, erect, branched panicles of wine-colored stems display flowers just above foliage beginning late spring with repeating panicles through the summer.
6. The new plant is vigorous and produces large broadly-mounded clumps.

BRIEF DESCRIPTION OF THE DRAWINGS

The photographs of the new plant demonstrate the overall appearance of the plant including the unique traits. The colors are as accurate as reasonably possible with color reproductions. Some slight variation of color may occur as a result of lighting quality, intensity, wavelength, and direction or reflection.

DETAILED BOTANICAL DESCRIPTION

Figure 1:
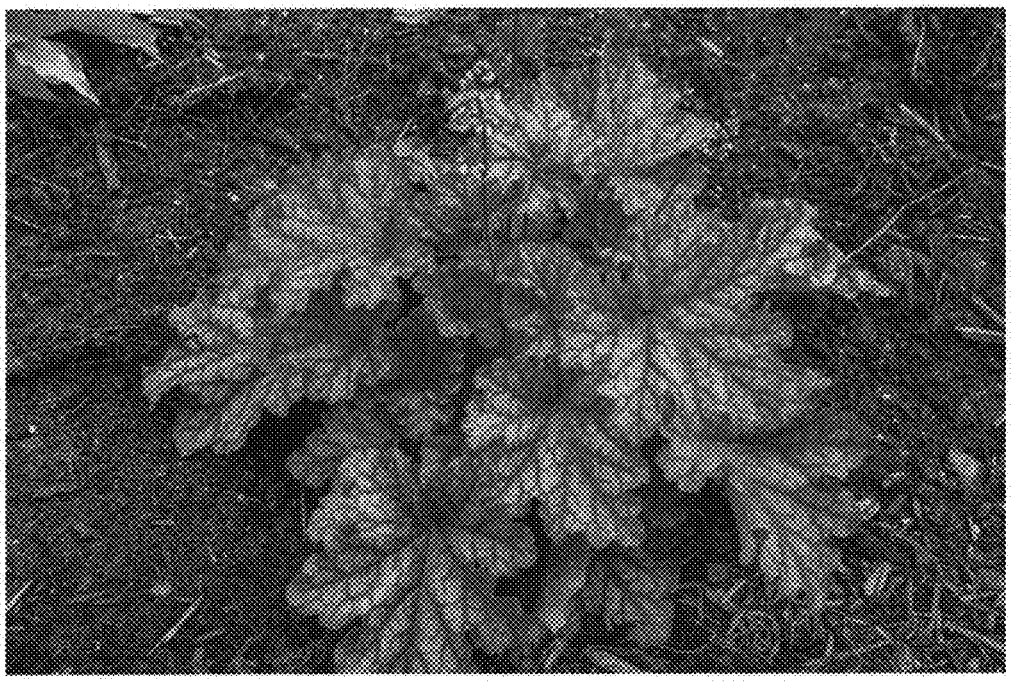
FIG. 1 shows a one-year-old plant with spring foliage before flowering.
Figure 2:
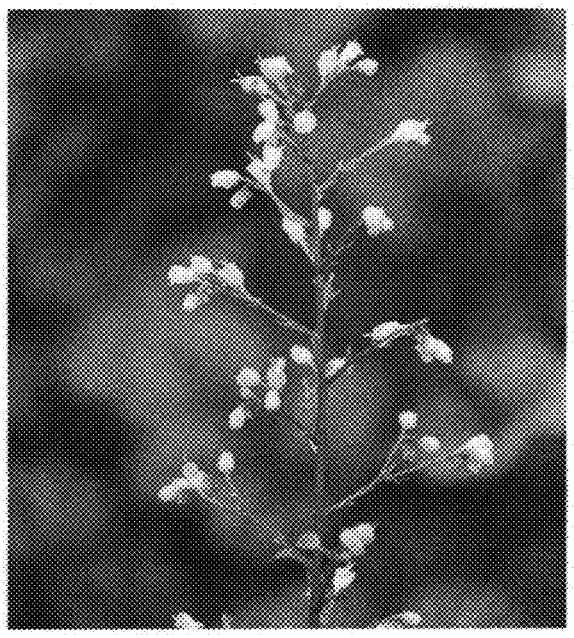
FIG. 2 shows a close-up of a flower panicle with buds and flowers from a one-year-old plant.
Figure 3:
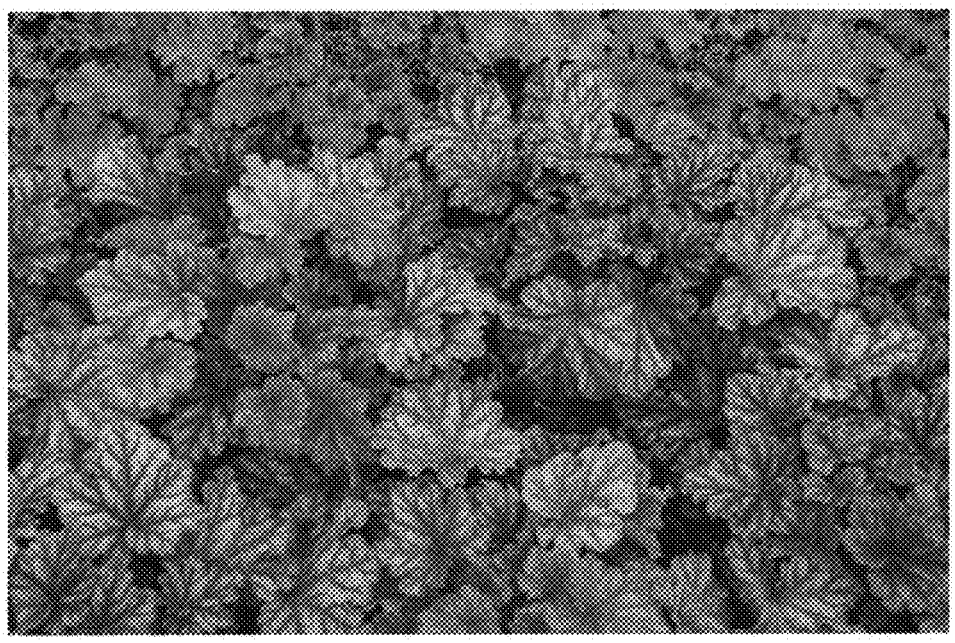
FIG. 3 shows two-year-old plants grown outdoors with early spring and transitioning foliage coloration.
Figure 4:
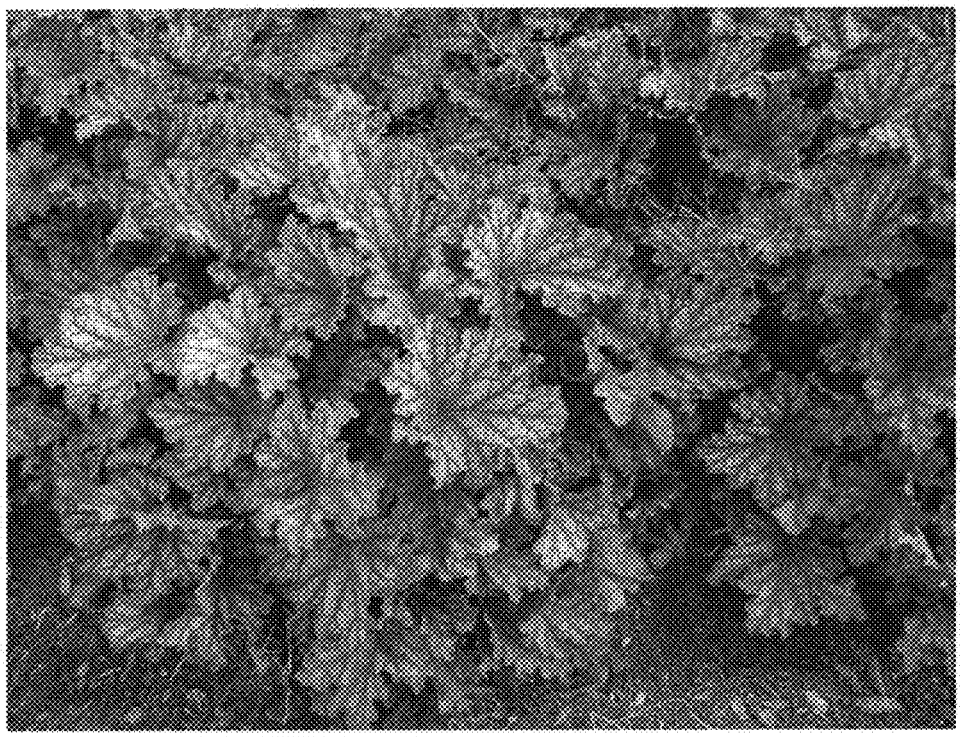
FIG. 4 shows two-year-old plants grown outdoors in mid-autumn foliage coloration.

The following description is based on a two-year-old plant growing in a partially shaded greenhouse in Zeeland, Mich., USA. The new plant has not been grown under all possible environments and may phenotypically appear different under different conditions such as light, temperatures, fertilizer, and water, without any difference in genotype. The color descriptions used are from the 2015 edition of The Royal Horticultural Society Colour Chart except where common dictionary terms are used.

Parentage: Female or seed parent was the unreleased proprietary hybrid 12-120-1 with 'Mocha' U.S. Plant Pat. No. 18,386 along with a proprietary selection of *Heuchera hallii* in the ancestry, the male or pollen parent was 'Paprika';

Plant habit: Hardy herbaceous perennial with basal rosette of foliage; dense broadly-mounded foliage about 36.0 cm tall and about 71.0 cm in diameter with scapes to about 57.0 cm long; with 10 stems per plant to about 7.0 cm long and 2.0 cm diameter at base, with about 14 to 16 leaves per stem; about 20 panicles per plant;

Roots: Fibrous, finely branched;

Growth rate: Rapid, rooting from cutting in two weeks and finishing in three-liter container in about two and a half months;

Foliage: Cordate; minutely and sparsely puberulent adaxial and abaxial; palmately shallowly lobed with five main lobes dissected less than one-eighth of the way to petiole; apex and lobe apices rounded and mucronulate; base cordate with basal lobes nearly overlapping to overlapping about 0.5 cm; margins crenate to mucronulate, micro-ciliolate, repand; weakly lustrous abaxial and matte adaxial; center flat; held upright near plant center to arching in outer leaves; moderately dense;

Leaf blade size: To about 14.5 cm wide and 15.5 cm long, average about 13.0 cm wide and 13.5 cm long;

Leaf color: Young initially emerging leaves adaxial nearest blend between RHS 46A and RHS 42B, abaxial nearest blend between RHS 47B and RHS 53B; still expanding young leaves adaxial more lighter grey than RHS 177C between the veins and surrounding the veins between RHS 178D and RHS 177D, still expanding leaves abaxial between RHS 182A and RHS 182B; mature mid-season leaves adaxial variable between nearest RHS 148A blended with RHS 177B surrounding the veins and the blend of RHS 148A and RHS 177B with silver overlay of nearest RHS 196A between the veins and other leaves with a blend between RHS 182B and RHS 183A surrounding the veins and nearest RHS 182D blended with RHS 190D as a silver overlay between the veins, abaxial mature mid-season leaves nearest blend between RHS 187C and RHS N186D; fall and winter color adaxial variable, nearest RHS 147A and RHS 146A blushed with RHS 187B to RHS 183A with partial silver overlay nearest RHS N187D between veins, fall and. winter color abaxial nearest RHS N77D;

Leaf quantity: Dense, about 150 per plant;

Veins: Palmate, hirsutulous abaxial and glabrous adaxial; costate abaxial, slightly impressed adaxial;

Vein color: Early emerging adaxial nearest blend between RHS 46A and RHS 42B, abaxial nearest RHS 186B; still expanding adaxial nearest RHS 182C, abaxial nearest RHS 182D; mid-season and flowering time main adaxial veins nearest RHS 176D near petiole and secondary veins near margin nearest RHS 147A, mid-season and flowering time main abaxial veins near petiole nearest RHS 182D and secondary veins near margin nearest RHS 187B; fall adaxial near petiole nearest RHS 146A and distally nearest RHS 147A, abaxial veins near petiole nearest RHS 182D and secondary veins near margin nearest RHS 187B;

Petiole: Terete, base amplexicaul; with pubescent hairs to about 2.0 mm long; to about 26.0 cm long and 3.5 mm wide before average about 20.0 cm long and about 3.0 mm diameter above stipule and 18.0 mm at base including stipule;

Petiole color: On early emerging leaves closer to RHS 60C than RHS 60B; on still expanding leaves nearest RHS 185D; flowering season mature leaf nearest RHS 187C; autumn season nearest RHS 178A;

Stipule: Flared at base of petiole; glaucous adaxial and abaxial with ciliolate margin; to about 2.0 cm long and about 18.0 mm wide at base; with two distal lateral projections of about 3.0 mm long in distal portion;

Stipule color: Young expanding leaf adaxial and abaxial nearest RHS 60C; mature leaf adaxial center with mixtures of RHS 146B and RHS 187C lateral margins nearest RHS 185D, abaxial nearest RHS N186C; lateral margin portions translucent;

Peduncle: Panicle; terete; stiff; pubescent; upright; densely branched; to about 52.0 cm long and 5.0 mm diameter at base, average about 48.0 cm tall and 4.5 mm diameter; about 20 per plant with up to about 345 flowers per panicle, average about 270; moderately-branched panicle with up to 22 branches up to about 5.0 cm long and 1.0 mm diameter decreasing distally, average 18 branches per panicle; lower branches about −45 degree above horizontal, becoming closer to 30 degrees above horizontal in distal 6.0 cm of panicle; flower density medium; with about 4 cauline leaves below flower, spaced about 7.5 cm apart;

Flowering longevity: Panicle effective for about three to four weeks; individual flowers about 5 days; self-cleaning;

Peduncle color: Nearest RHS 187B becoming nearest RHS 187A distally;

Cauline leaves: Palmate; coarsely dentate margin; puberulent abaxial and adaxial; petiolate; blade about 21.0 mm across and 20.0 mm long, petiole about 7.0 mm long and 5.0 mm wide with stipule; with pair of stipules at base about 5.0 mm long; cauline leaves, petiole and stipule decreasing distally to become bracts subtending peduncle branches; stipules lanceolate with acute apex, truncate base and ciliate margin;

Cauline leaf color: Adaxial blade blend nearest RHS 146A and RHS N167A, abaxial between RHS 182A and RHS 182B; petiole nearest RHS 178A abaxial and adaxial, and stipule adaxial and abaxial nearest RHS 182A;

Pedicel: Terete, pubescent; to about 5.0 mm long and 0.5 mm diameter, average about 3.0 mm long and 0.5 mm diameter; attitude outwardly to slightly upwardly;

Pedicel color: Nearest RHS 187C lightening with age;

Buds one day prior to opening: Ellipsoid; rounded apex and attenuate base; micro-glandular; about 5.5 mm long and 2.5 mm diameter;

Bud color one day prior to opening: Nearest RHS N155B;

Flower: Perfect; campanulate; actinomorphic; about 7.0 mm long to tip of exserted style and 3.0 mm in diameter at corolla apex; medium density;

Flower attitude: Mostly outwardly;

Calyx: Five, apex rounded, base fused in proximal 2.5 mm to form hypanthium; micro-glandular abaxial, glabrous adaxial; about 5.5 mm long and.4.0 mm wide at apex;

Sepals: Five; lanceolate; acute apex, fused in basal 2.5 mm; to about 5.0 mm long and 1.5 mm wide at fusion;

Sepal color: Abaxial apex nearest RHS 186C and middle nearest RHS N155B and base nearest RHS 186B; adaxial apex and longitudinal middle blushed with nearest RHS 64A and base nearest RHS N155B;

Petals: Five; oblanceolate to spatulate; subacute apex and attenuate base; entire; glabrous abaxial and adaxial; about 3.5 mm long and 1.0 mm wide in middle;

Petal color: Abaxial and adaxial nearest RHS NN155D with very faint blush of light pink;

Androecium: Five adnate to adaxial sepal about 1.0 mm above base;

*Filaments*.—Five, thin, glabrous; about 2.5 mm long and less than 0.3 mm diameter; color nearest RHS NN155B.

*Anthers*.—Ellipsoidal, distinct, basifixed, longitudinal; about 0.5 mm long and about 0.3 mm across; color nearest RHS 16C.

*Pollen*.—Rare; color nearest RHS 17B.

Gynoecium: One, two-beaked; half-inferior; bifid style with pistil split at ovary; about 6.0 mm long;

*Style*.—Bifid; split apart at apex of ovary; exserted; about 3.5 mm long and about 0.5 mm diameter; color nearest RHS NN155B.

*Stigma*.—Acute apex, about 0.1 mm diameter; color nearest RHS N155C.

*Ovary*.—Half-inferior, about 2.0 mm long and 2.0 mm diameter; ellipsoidal to globose, base rounded; color nearest RHS 157D.

Fruit: Small two-beaked capsule; about 3.0 mm long and 2.5 mm across; drying to blend between RHS 199A and RHS N199C;

Seeds: Abundant; slightly flattened ellipsoid; about 0.7 mm long, 0.5 mm across and about 0.3 mm thick; color nearest RHS 202A;

Disease and pest tolerance: The new plant grows best with ample moisture and drainage in either part sun or full shade. The new plant is resistant to high heat and humidity. Cold hardy from USDA zones 4 to 9. Other resistance and tolerance, including the genus and species of diseases, outside of that normal for *Heuchera* is not known or claimed.

It is claimed:

1. A new and distinct coral bells plant named *Heuchera* 'Peachberry Ice' as herein described and illustrated.

* * * * *